(12) United States Patent
Daum et al.

(10) Patent No.: US 6,751,502 B2
(45) Date of Patent: Jun. 15, 2004

(54) CARDIAC RHYTHM MANAGEMENT SYSTEM WITH DEFIBRILLATION THRESHOLD PREDICTION

(75) Inventors: Douglas R. Daum, Oakdale, MN (US); Weimin Sun, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 40 days.

(21) Appl. No.: 09/808,419

(22) Filed: Mar. 14, 2001

(65) Prior Publication Data

US 2002/0133206 A1 Sep. 19, 2002

(51) Int. Cl.[7] .................................................. A61N 1/39
(52) U.S. Cl. ............................................... 607/8; 607/5
(58) Field of Search .............................. 607/4, 5, 8, 27, 607/28

(56) References Cited

U.S. PATENT DOCUMENTS

| | | | |
|---|---|---|---|
| 5,318,597 A | 6/1994 | Hauck et al. ................. 607/20 |
| 5,397,336 A * | 3/1995 | Hirschberg et al. ............. 607/6 |
| 5,531,770 A | 7/1996 | Kroll et al. ..................... 607/8 |
| 5,540,724 A | 7/1996 | Cox ............................... 607/8 |
| 5,683,431 A * | 11/1997 | Wang .......................... 607/28 |
| 5,978,705 A * | 11/1999 | KenKinght et al. ............. 607/5 |
| 5,999,852 A | 12/1999 | Elabbady et al. ............... 607/8 |
| 6,076,015 A | 6/2000 | Hartley et al. ................. 607/20 |
| 6,353,761 B1 * | 3/2002 | Conley et al. ................. 607/28 |

OTHER PUBLICATIONS

Bessho, R., et al., "Measurement of the upper limit of vulnerability during defibrillator implantation can substitute defibrillation threshold measurement", *The International Journal of Artificial Organs*, 21 (3), pp. 151–160, (1998).

Church, T., et al., "A Model to Evaluate Alternative Methods of Defibrillation Threshold Determination", *PACE, 11*, pp. 2002–2007, (Nov. 1988).

(List continued on next page.)

*Primary Examiner*—Carl Layno
(74) *Attorney, Agent, or Firm*—Schwegman, Lundberg, Woessner & Kluth, P.A.

(57) ABSTRACT

A cardiac rhythm management device predicts defibrillation thresholds without any need to apply defibrillation shocks or subjecting the patient to fibrillation. Intravascular defibrillation electrodes are implanted in a heart. By applying a small test energy, an electric field near one of the defibrillation electrodes is determined by measuring a voltage at a sensing electrode offset from the defibrillation electrode by a known distance. A desired predetermined minimum value of electric field at the periphery of the heart is established. A distance between one of the defibrillation electrodes and the heart periphery is measured, either fluoroscopically or by measuring a voltage at an electrode located at or near the heart periphery. Using the measured electric field and the measured distance to the periphery of the heart, the defibrillation energy needed to obtain the desired electric field at the heart periphery is estimated. This estimation is based on an elliptical model of the electric field distribution around the dipole foci formed by the defibrillation electrodes, or other suitable electric field model.

57 Claims, 10 Drawing Sheets

OTHER PUBLICATIONS

Eason, J., et al., "Influence of Anisotropy on Local and Global Measures of Potential Gradient in Computer Models of Defibrillation", *Annals of Biomedical Engineering*, 26, pp. 840–849, (1998).

Ellenbogen, K.A., et al., "Immediate Reproducibility of Upper Limit of Vulnerability Measurements in Patients Undergoing Transvenous Implantable Cardioverter Defibrillator Implantation", *Journal of Cardiovascular Electrophysiology*, 9 (6), pp. 588–595, (Jun. 1998).

Martin, D.J., et al., "Upper Limit of Vulnerability Predicts Chronic Defibrillation Threshold for Transvenous Implantable Defibrillators", *Journal of Cardiovascular Electrophysiology*, 8 (3), pp. 241–248, (Mar. 1997).

Min, X., et al., "Finite element analysis of defibrillation fields in a human torso model for ventricular defibrillation", *Progress in Biophysics & Molecular Biology*, 69, pp. 353–386, (1998).

Pendekanti, R., et al., "Spatial Potential and Current Distributions Along Transvenous Defibrillation Electrodes: Variation of Electrode Characteristics", *Annals of Biomedical Engineering*, 24, pp. 156–167, (1996).

Schimpf, P.H., et al., "Effects of electrode interface impedance of finite element models of transvenous defibrillation", *Medical & Biological Engineering & Computing*, pp. 713–719, (Sep. 1995).

Swerdlow, C.D., et al., "Comparative Reproducibility of Defibrillation Threshold and Upper Limit of Vulnerability", *PACE*, 19, pp. 2103–2111, (Dec. 1996).

Swerdlow, C.D., et al., "Programming of Implantable Cardioverter–Defibrillators on the Basis of the Upper Limit of Vulnerability", *Circulation*, 95 (6), pp. 1497–1504, (Mar. 18, 1997).

Wang, Y., et al., "Analysis of Defibrillation Efficacy from Myocardial Voltage Gradients with Finite Element Modeling", *IEEE Transactions on Biomedical Engineering*, 46 (9), pp. 1025–1036, (1999).

Sun, Weimin, et al., "DFT Test Via Pacing Measurements without VF Induction and Shocking", *PACE*, vol. 23, Abstract No. 235,(Apr. 2000),1 pg.

* cited by examiner

DEFIBRILLATION THRESHOLD VOLTAGE LOOKUP TABLE
(VOLTS)

D2−D1 (CM)

| Fractional Tip Voltage Parameter | 1 | 1.2 | 1.4 | 1.6 | 1.8 | 2 | 2.2 | 2.4 | 2.6 | 2.8 | 3 | 3.2 | 3.4 | 3.6 | 3.8 | 4 | 4.2 | 4.4 | 4.6 | 4.8 | 5 |
|---|---|---|---|---|---|---|---|---|---|---|---|---|---|---|---|---|---|---|---|---|---|
| 30.0 | 113 | 131 | 142 | 159 | 181 | 194 | 215 | 239 | 257 | 280 | 304 | 327 | 353 | 377 | 403 | 432 | 457 | 488 | 520 | 552 | 590 |
| 32.5 | 115 | 132 | 144 | 161 | 182 | 197 | 217 | 240 | 258 | 281 | 304 | 327 | 353 | 377 | 403 | 432 | 457 | 488 | 520 | 552 | 590 |
| 35.0 | 117 | 134 | 148 | 165 | 185 | 201 | 221 | 243 | 262 | 284 | 307 | 331 | 356 | 380 | 407 | 434 | 461 | 491 | 522 | 553 | 591 |
| 37.5 | 121 | 137 | 153 | 170 | 189 | 207 | 227 | 248 | 269 | 291 | 314 | 338 | 363 | 388 | 415 | 442 | 470 | 499 | 530 | 561 | 593 |
| 40.0 | 126 | 141 | 159 | 176 | 195 | 215 | 235 | 256 | 278 | 301 | 324 | 349 | 374 | 400 | 428 | 455 | 484 | 514 | 545 | 576 | 604 |
| 42.5 | 131 | 147 | 166 | 184 | 203 | 224 | 245 | 266 | 290 | 313 | 337 | 363 | 389 | 416 | 445 | 473 | 504 | 534 | 566 | 598 | 624 |
| 45.0 | 137 | 154 | 174 | 193 | 213 | 235 | 257 | 279 | 304 | 328 | 353 | 381 | 408 | 436 | 467 | 496 | 529 | 561 | 594 | 627 | 653 |
| 47.5 | 145 | 162 | 183 | 203 | 224 | 248 | 271 | 294 | 321 | 347 | 373 | 402 | 431 | 461 | 493 | 525 | 559 | 593 | 628 | 664 | 693 |
| 50.0 | 153 | 171 | 194 | 215 | 237 | 262 | 287 | 312 | 341 | 368 | 396 | 427 | 458 | 490 | 524 | 558 | 595 | 631 | 669 | 708 | 740 |
| 52.5 | 162 | 182 | 205 | 228 | 252 | 278 | 306 | 332 | 363 | 392 | 422 | 455 | 489 | 523 | 560 | 596 | 636 | 676 | 717 | 759 | 797 |
| 55.0 | 172 | 194 | 218 | 243 | 269 | 296 | 326 | 355 | 387 | 419 | 452 | 487 | 524 | 561 | 600 | 640 | 682 | 726 | 771 | 817 | 864 |
| 57.5 | 183 | 207 | 232 | 259 | 288 | 315 | 348 | 380 | 414 | 449 | 485 | 522 | 563 | 602 | 645 | 689 | 734 | 782 | 832 | 883 | 940 |
| 60.0 | 195 | 222 | 247 | 276 | 308 | 337 | 373 | 408 | 444 | 482 | 521 | 561 | 606 | 649 | 694 | 743 | 790 | 845 | 899 | 955 | 1025 |
| 62.5 | 208 | 237 | 263 | 295 | 330 | 359 | 399 | 439 | 476 | 518 | 560 | 604 | 653 | 699 | 748 | 802 | 853 | 913 | 973 | 1035 | 1119 |
| 65.0 | 221 | 254 | 280 | 315 | 354 | 384 | 428 | 471 | 510 | 556 | 603 | 649 | 704 | 754 | 806 | 866 | 920 | 987 | 1053 | 1122 | 1223 |
| 67.5 | 236 | 272 | 298 | 336 | 379 | 410 | 458 | 507 | 548 | 598 | 649 | 699 | 759 | 813 | 869 | 935 | 993 | 1067 | 1140 | 1217 | 1336 |
| 70.0 | 251 | 292 | 317 | 359 | 407 | 438 | 491 | 545 | 587 | 642 | 698 | 752 | 818 | 876 | 937 | 1009 | 1071 | 1154 | 1234 | 1318 | 1458 |

FIG. 3

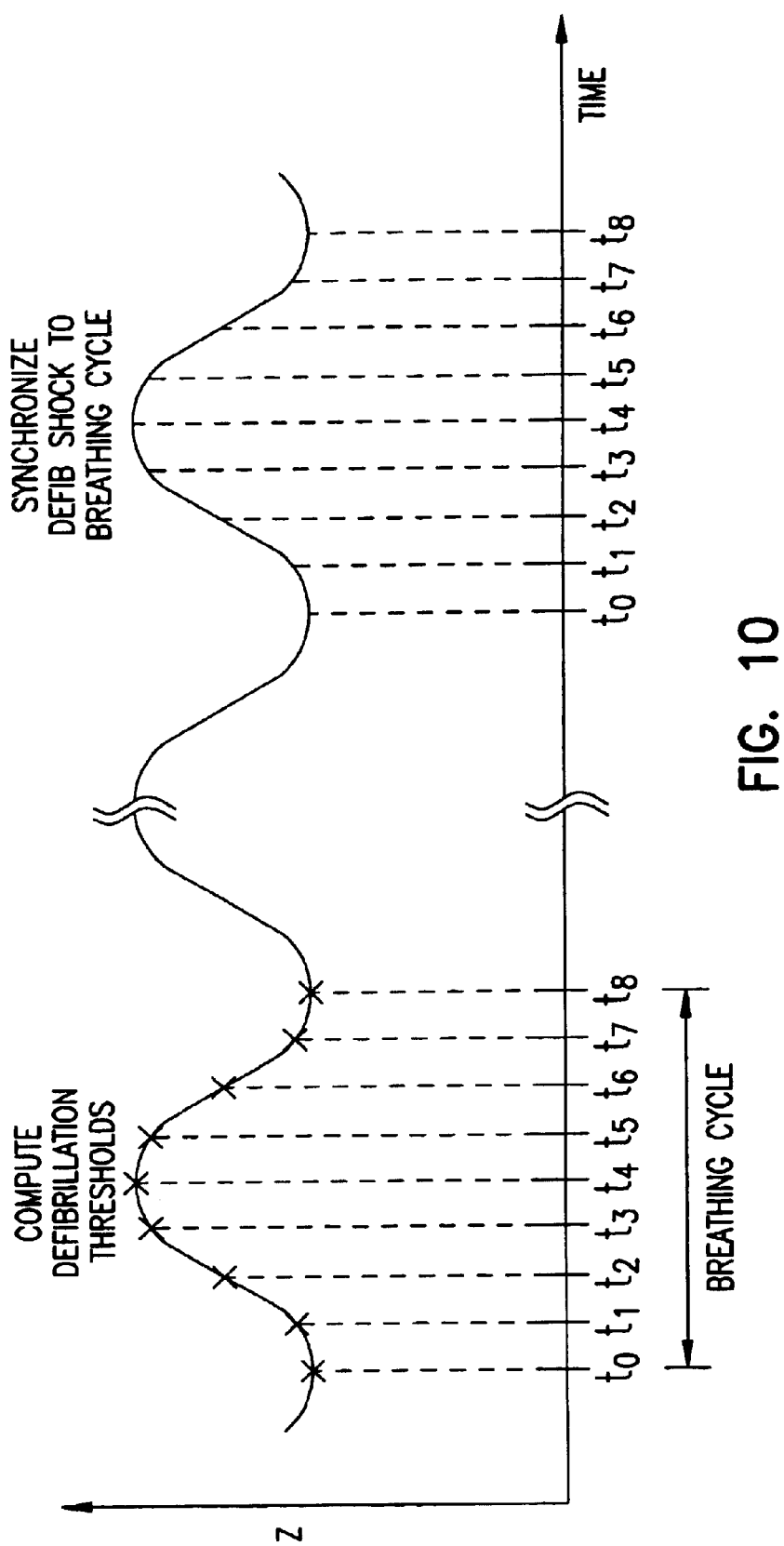

CARDIAC RHYTHM MANAGEMENT SYSTEM WITH DEFIBRILLATION THRESHOLD PREDICTION

TECHNICAL FIELD

The present system relates generally to cardiac rhythm management systems and particularly, but not by way of limitation, to a system providing, among other things, defibrillation threshold prediction.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the determination of the threshold energy required, for a particular defibrillation shock waveform, to reliably convert a tachyarrhythmia into a normal heart rhythm. Ventricular and atrial fibrillation are probabilistic phenomena that observe a dose-response relationship with respect to shock strength. The ventricular defibrillation threshold (VDFT) is the smallest amount of energy that can be delivered to the heart to reliably revert ventricular fibrillation to a normal rhythm. Similarly, the atrial defibrillation threshold (ADFT) is the threshold amount of energy that will terminate an atrial fibrillation. Such defibrillation thresholds vary from patient to patient, and may even vary within a patient depending on the placement of the electrodes used to deliver the therapy. In order to ensure the efficacy of such therapy and to maximize the longevity of the battery source of such therapy energy, the defibrillation thresholds must be determined so that the defibrillation energy can be safely set above the threshold value but not at so large of a value so as to waste energy and shorten the usable life of the implanted device.

One technique for determining the defibrillation threshold is to induce the targeted tachyarrhythmia (e.g., ventricular fibrillation), and then apply shocks of varying magnitude to determine the energy needed to convert the arrhythmia into a normal heart rhythm. However, this requires imposing the risks and discomfort associated with both the arrhythmia and the therapy. Electrical energy delivered to the heart has the potential to both cause myocardial injury and subject the patient to pain. Moreover, if defibrillation thresholds are being obtained in order to assist the physician in determining optimal lead placement, these disadvantages are compounded as the procedure is repeated for different potential lead placements.

Another technique for determining the defibrillation threshold, referred to as the "upper limit of vulnerability" technique, a patient in a state of normal heart rhythm is shocked during the vulnerable (T-wave) period of the cardiac cycle during which time the heart tissue is undergoing repolarization. Shocks of varying magnitude are applied until fibrillation is induced. Of course, after such fibrillation is induced, the patient must be again shocked in order to interrupt the arrhythmia and reestablish a normal heart rhythm. In this technique, the corresponding fibrillation-inducing shock magnitude is then related to a defibrillation threshold energy using a theoretical model. The upper limit of vulnerability technique also suffers from imposing the risks and discomfort associated with both the arrhythmia and the shock therapy. Moreover, because of the discomfort associated with the fibrillation and countershocks, the patient is typically sedated under general anesthesia, which itself has some additional risk and increased health care cost. For these and other reasons, there is a need to estimate defibrillation thresholds without relying on a defibrillation shock to induce or terminate an actual arrhythmia.

SUMMARY

The present system provides, among other things, a cardiac rhythm management system that predicts defibrillation thresholds without any need to apply defibrillation shocks or subjecting the patient to fibrillation. In one embodiment, the system provides a method that includes delivering a nondefibrillating and nonfibrillation-inducing test energy to a heart, detecting a resulting output signal based on the test energy and a heart characteristic, and estimating a defibrillation threshold, based on the output signal, for a portion of the heart to be defibrillated.

In one embodiment, the system includes first and second electrodes configured for association with a heart. A test energy module is coupled to the second electrode, for delivering a nondefibrillating and nonfibrillation-inducing test energy to the heart. A response signal module is coupled to the first and second electrodes for detecting responses to the test energy. A controller is coupled to the response signal module. The controller estimates a defibrillation threshold energy based on a predetermined desired defibrillation electric field at a distal portion of the heart tissue to be defibrillated and a distance from the second electrode to the distal portion of the heart tissue, and an indication of the electric field near the second electrode. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 3 is a lookup table illustrating estimating defibrillation threshold voltages based on an indication of electric field near a defibrillation electrode and a distance therefrom.

FIG. 10 is a flow chart illustrating another embodiment for modifying the delivery of a defibrillation shock or other therapy based on previously acquired defibrillation threshold data over a range of another patient characteristic.

DETAILED DESCRIPTION

Figure 1:
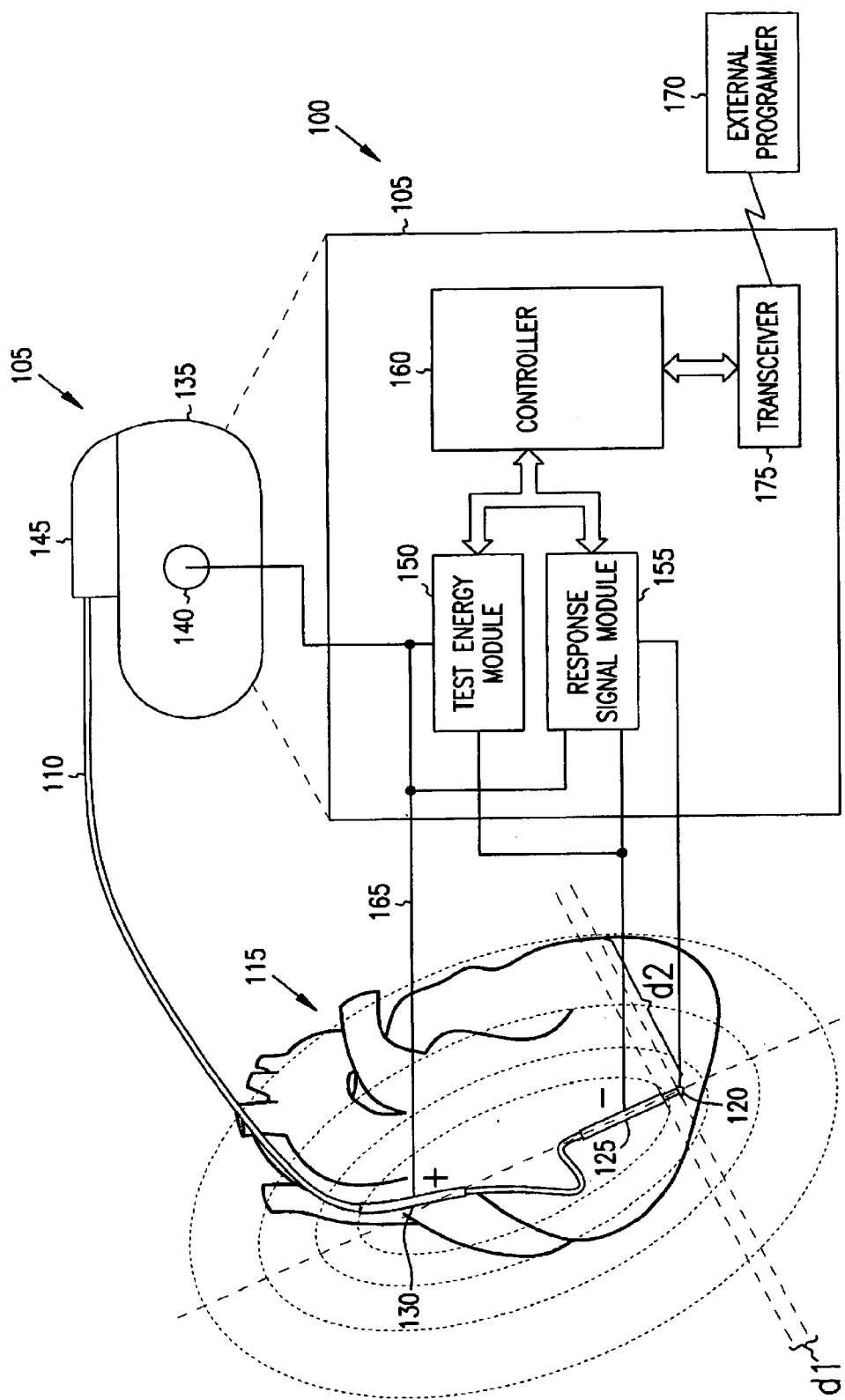
FIG. 1 is a schematic/block diagram illustrating portions of the present cardiac rhythm management system and portions of an environment of use.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

The present methods and apparatus will be described in applications involving implantable medical devices including, but not limited to, implantable cardiac rhythm management systems such as pacemakers, cardioverter/defibrillators, pacer/defibrillators, biventricular or other multi-site coordination devices, and drug delivery systems for managing cardiac rhythm. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

EXAMPLE A

FIG. 1 is a schematic/block diagram illustrating generally, by way of example, and not by way of limitation, one embodiment of portions of the present cardiac rhythm management system 100 and portions of an environment in which the present system 100 and associated techniques are used. System 100 includes, among other things, cardiac rhythm management device 105 and leadwire ("lead") 110 for communicating signals between device 105 and a portion of a living organism, such as heart 115. Embodiments of device 105 include, but are not limited to, bradycardia and antitachycardia pacemakers, cardioverters, defibrillators, combination pacemaker/defibrillators, drug delivery devices, and any other implantable or external cardiac rhythm management apparatus capable of providing therapy to heart 115.

In this example, lead 110 includes multiple electrodes, and individual conductors for independently communicating an electrical signal from each electrode to device 105. In one embodiment, these electrodes include a right ventricular (RV) tip-type electrode 120 at the distal end of lead 110. In one example embodiment, electrode 120 has a macroscopic surface area that is approximately between 1 mm$^2$ and 20 mm$^2$, inclusive. RV tip electrode 120 is configured to be positioned in the right ventricle at or near its apex or at any other suitable location. RV shock electrode 125 is located on the lead at a known predetermined distance, d1, from RV tip electrode 120, as measured from the edges of these electrodes. RV shock electrode 125 is typically located in the right ventricle or at any other suitable location. In one embodiment, RV shock electrode 125 is a coil-type electrode having a macroscopic surface area that is approximately between 2 cm$^2$ and 20 cm$^2$, inclusive. Superior vena cava (SVC) electrode 130 is located in a portion of the superior vena cava, the right atrium, or both, or at any other suitable location. In one embodiment, SVC electrode 130 is a coil-type electrode having a macroscopic surface area that is approximately between 2 cm$^2$ and 20 cm$^2$, inclusive. Although RV tip electrode 120, RV shock electrode 125, and SVC electrode 130 are particularly described above with respect to structural characteristics and locations for disposition, it is understood that these electrodes may take the form of any of the various cardiac electrodes known in the art (e.g., epicardial patch electrodes) and may be positioned elsewhere for association with heart 115 or other tissue.

In one embodiment, device 105 includes a hermetically sealed housing 135, formed from a conductive metal, such as titanium, and implanted within a patient such as within the pectoral or abdominal regions. In this example, housing 135 (also referred to as a "case" or "can") is substantially covered over its entire surface by a suitable insulator, such as silicone rubber, except for at a window that forms a "case" or "can" or "housing" electrode 140. As understood by one of ordinary skill in the art, housing electrode 140, although not located in the heart, is associated with the heart for providing what is sometimes referred to as "unipolar" sensing or pacing or defibrillation therapy. In one embodiment, a header 145 is mounted on housing 135, such as for receiving lead 110. Header 145 is formed of an insulative material, such as molded plastic. Header 145 also includes at least one receptacle, such as for receiving lead 110 and electrically coupling conductors of lead 110 to device 105. Header 145 may also include one or more additional electrodes. In this example, ventricular fibrillation is treated by delivering a defibrillation shock between RV shock electrode 125 and the commonly connected combination of SVC electrode 130 and housing electrode 140; a defibrillation threshold is also obtained with SVC electrode 130 and housing electrode 140 connected in common. However, it is understood that these electrodes could be differently configured, such as for delivering defibrillation therapy between RV shock electrode 125 and housing electrode 140.

FIG. 1 also illustrates, in an exploded view block diagram form, portions of device 105. It is understood that device 105 is coupled to heart 115 via lead 110; the illustrated connection lines associated with the exploded view are illustrative only. In FIG. 1, test energy module 150 generates an energy from which a heart characteristic can be determined via response signal module 155. From these measurements, a defibrillation threshold is computed, for example, either by a defibrillation threshold estimation module in controller 160, which itself is in device 105, or in external programmer 170, which is communicatively coupled to a transmitter or receiver in device 105, such as transceiver 175. The defibrillation estimation module is implemented as a sequence of steps carried out on a microprocessor or other microsequencer, in analog, digital, or mixed-signal hardware, or in any suitable hardware and/or software configuration. In this example, SVC electrode 130 is electrically connected in common with housing electrode 140, at node 165, and also coupled to each of test energy module 150 and response signal module 155.

Figure 2:
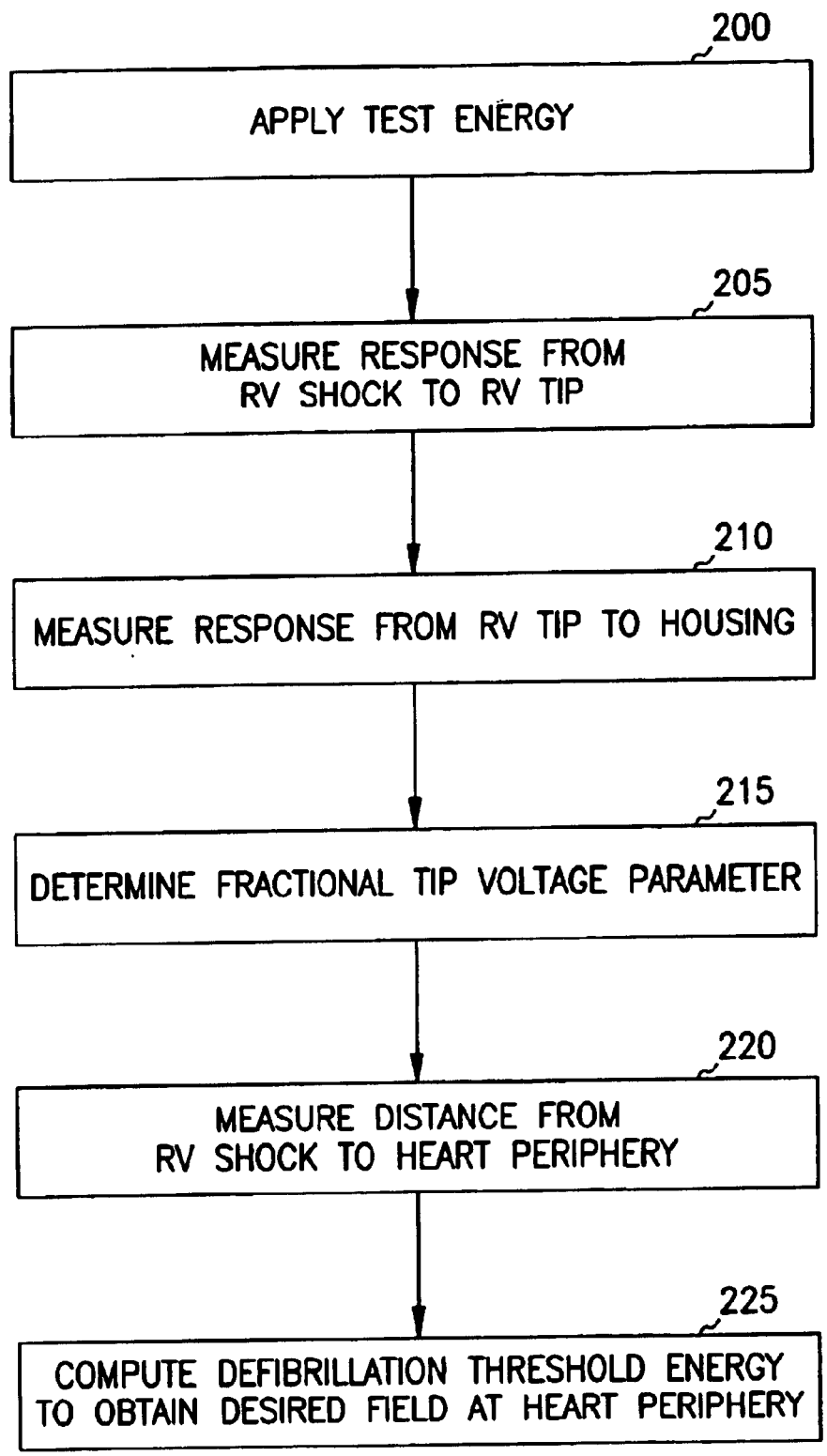
FIG. 2 is a flow chart illustrating a technique for estimating defibrillation thresholds such as using the system of FIG. 1.

FIG. 2 is a flow chart illustrating generally, by way of example, but not by way of limitation, one embodiment of a technique for estimating defibrillation thresholds such as using the system 100 of FIG. 1. This technique is carried out as executable instructions, such as by controller 160, but it need not be carried out in the exact sequence illustrated in FIG. 2. At step 200, test energy module 150 applies a test energy by providing a drive current of predetermined magnitude (e.g., approximately 30 to 1000 microamperes, inclusive) between RV shock electrode 125 and housing electrode 140. In one example, this drive current is delivered in a continuous or pulsed/strobed 25 kHz waveform; in this example the 30 to 1000 microamperes current magnitudes are the zero-to-peak values of this test waveform. However, it is understood that the technique could use any other test energy that does not defibrillate the associated heart tissue and does not induce fibrillation, such as when the energy is delivered during a cardiac repolarization or by using a non-painful stimulus such as a pacing pulse (e.g., amplitude approximately between 0.1 Volt and 10 Volts, inclusive, duration approximately between 0.05 milliseconds and 10 milliseconds, inclusive). In one embodiment, the test energy typically has an energy less than 10 milliJoules, while typical defibrillation threshold energies are between 1 and 40 Joules. The test energy may be delivered from either a current source or a voltage source.

At step 205, response signal module 155 measures a response voltage V1 between RV shock electrode 125 and RV tip electrode 120. At step 210, response signal module 155 also measures a response voltage V2 between RV tip electrode 120 and housing electrode 140. One such embodiment of providing a test current and sensing a resulting voltage is described in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety, including its incorporation by reference of Hauck et al., U.S. Pat. No. 5,318,597 entitled "RATE ADAPTIVE CARDIAC RHYTHM MANAGEMENT DEVICE CONTROL ALGORITHM USING TRANS-THORACIC VENTILATION, also assigned to Cardiac Pacemakers, Inc. Although the Hartley et al. patent is directed toward providing a test current and sensing a resulting voltage to measure transthoracic impedance, those same techniques and structures for carrying out such techniques, including the use of a continuous or pulsed/strobed high frequency carrier signal (e.g., at a frequency that is approximately between 1 kHz and 100 kHz, inclusive), are also applicable here. Such techniques are employed either using the electrode configuration illustrated in FIG. 1, or using the electrode configuration described or incorporated by reference in the Hartley et al patent, or by using any other suitable electrode configuration that disposes electrodes for association with heart 115 for providing a test signal and/or detecting a response signal.

In this example, at step 215, a fractional tip voltage parameter $V2/(V1+V2)$ is determined by controller 160 or external programmer 170. This fractional tip voltage parameter provides a measured indication of the electric field distribution near RV shock electrode 125, because it relates to a voltage drop over a known distance d1.

In this example, at step 220, the attending physician or other user measures a distance d2 from the RV shock electrode the outer periphery of the left ventricular apex. In one embodiment, this distance is measured by viewing an image of the heart on a fluoroscope or other imaging apparatus, using the known distance d1 to assess the distance d2. Based on the distance d2 and the fractional tip voltage parameter, a defibrillation threshold is estimated, at step 225, using a model of electric field distribution (for example, having foci at RV shock electrode 125 and at SVC electrode 130, as illustrated in this example by the elliptical lines superimposed on heart 115 in FIG. 1) that provides a desired electric field magnitude throughout the heart, including its periphery.

In one embodiment, a generalized electric field distribution for the particular lead electrode configuration is calculated a priori using the known lead electrode geometry and the boundary element method, or similar method, to solve the electric field Laplace equation. In one example, commercially available finite element analysis software is used to solve the electric field distribution for the particular electrode arrangement. A resulting generalized equation describing the electric field is then obtained using a cubic fit.

For a particular electrode configuration, the measured voltage at tip electrode 120 may be different from that obtained from the generalized electric field equation for the modeled electrode geometry, for example, because of a small variation in the distance between tip electrode 120 and coil electrode 125, and/or because of the particular tissue and/or blood conductivity characteristics of the patient. To obtain additional accuracy, these small variations are accounted for by scaling or otherwise calibrating the generalized electric field equation such that it obtains substantially the same electric field at the tip electrode 120 as the measured electric field at tip electrode 120, an indication of which is given by the fractional tip voltage parameter. Using the resulting calibrated electric field equation and measured distance to the heart periphery, the electric field obtained at the heart periphery in response to the test voltage is calculated. The defibrillation threshold voltage, then, is calculated by scaling the test voltage delivered at coil electrode 125 by the ratio of the desired electric field at the heart periphery needed for successful defibrillation (e.g., 5 Volts/cm) to the extrapolated value of electric field at the heart periphery obtained from the calibrated electric field equation in response to the test voltage stimulus.

In this example, it has been assumed that a minimum electric field magnitude of 5 Volts/cm at the left ventricular periphery of heart 115 (at a distance d2 away from RV shocking electrode 125) is required to convert ventricular fibrillation into a normal heart rhythm (e.g., with a 50% probability). A more conservative user might select a larger predetermined desired electric field intensity (e.g., 6 V/cm) at the heart periphery. Moreover, other experimental data might indicate that a lower electric field intensity (e.g., 4 V/cm) is sufficient to obtain a successful defibrillation. It is understood that the present system and techniques are applicable and may be used in conjunction with any desired electric field intensity at the distal point (from the defibrillation electrode) of the tissue being defibrillated.

For ease of use, such as in an implantable device, the defibrillation threshold voltage is, in one embodiment, stored in a lookup table in a memory device. FIG. 3 illustrates generally, by way of example, but not by way of limitation, one embodiment of such a lookup table. In this embodiment, the defibrillation threshold voltage needed to obtain a 5 Volts/cm electric field at the left ventricular heart periphery is given as a function of: (1) the measured distance d2 less the known distance d1; and (2) the fractional tip voltage parameter. Thus, the lookup table in FIG. 3 represents solving the electric field distribution for a particular lead geometry and a range of various heart sizes, calibrating the resulting cubic-fitted electric field equations according to different measured values of electric field as indicated by the range of fractional tip voltage parameters, and obtaining the corresponding defibrillation threshold voltage by scaling the test voltage by the ratio of the "safe" value of electric field at the heart periphery to the extrapolated value of the electric field at the heart periphery as obtained from the calibrated electric field equation in response to the test voltage delivered from the defibrillation coil electrode 120. Thus, FIG. 3 indicates, for example, for a measured distance, (d2–d1), of 3.4 cm and a fractional tip voltage parameter of 45.0, then the predicted defibrillation threshold voltage given by the table in FIG. 3 is 408 Volts.

In this way, the detected electric field (represented by the fractional tip voltage parameter) associated with the detected voltage between RV shock electrode 125 and SVC electrode 130 in response to the test energy is scaled upward to ensure an adequate minimum electric field at the heart periphery (and, therefore, an adequate electric field throughout that portion of the heart tissue being defibrillated). The associated scaled voltage that provides the desired electric field at the heart periphery is deemed the appropriate defibrillation threshold voltage.

Stated differently, in summary, for a given defibrillation waveform, the corresponding defibrillation threshold voltage is obtained as follows. An elliptical or other (e.g., spherical, quadratic, exponential, polynomial, or other approximation of electric field) electric field model is used to extrapolate the electric field at a distal portion of the heart tissue to be defibrillated (e.g., the left ventricular periphery in this example) based on the electric field measured near the defibrillation electrode (e.g., the RV shock electrode 125 in this example) and the measured distance d2 to the distal portion of the heart tissue to be defibrillated. The defibrillation threshold is obtained by scaling the measured voltage at the defibrillation electrode by the ratio of the desired defibrillation electric field at the distal portion of the heart to be defibrillated to the test value of electric field at that distal portion as obtained by the previous measurement and modeled extrapolation. For this particular example, then, the estimated defibrillation threshold voltage, VDFT, is represented by $VDFT = V_{125} * (E_{LV,DESIRED}/E_{LV, MODEL})$; in this equation, $V_{125}$ is the voltage measured (or calculated) at RV shock electrode 125 in response to the test current, $E_{LV, DESIRED}$ is the desired electric field at the left ventricular periphery for proper defibrillation (in this case, assumed to be 5 V/cm), and $E_{LV, MODEL}$ is the electric field at the left ventricular periphery based on the electric field measurement near RV shock electrode 125 and the extrapolation over the distance d2 using the elliptical or other electric field model.

It should be understood that the defibrillation threshold voltage could further be scaled upward to provide a safety margin of additional defibrillation energy. Moreover, although this example described measuring d2 from the RV shocking electrode 125 to the left ventricular periphery, it is understood that the measurement d2 may be performed between any electrode used to deliver defibrillation energy to any portion of heart 115 and a distal portion of the heart tissue that is farthest from the defibrillation electrode but for which an adequate defibrillation electric field is desired.

EXAMPLE B

Figure 4:
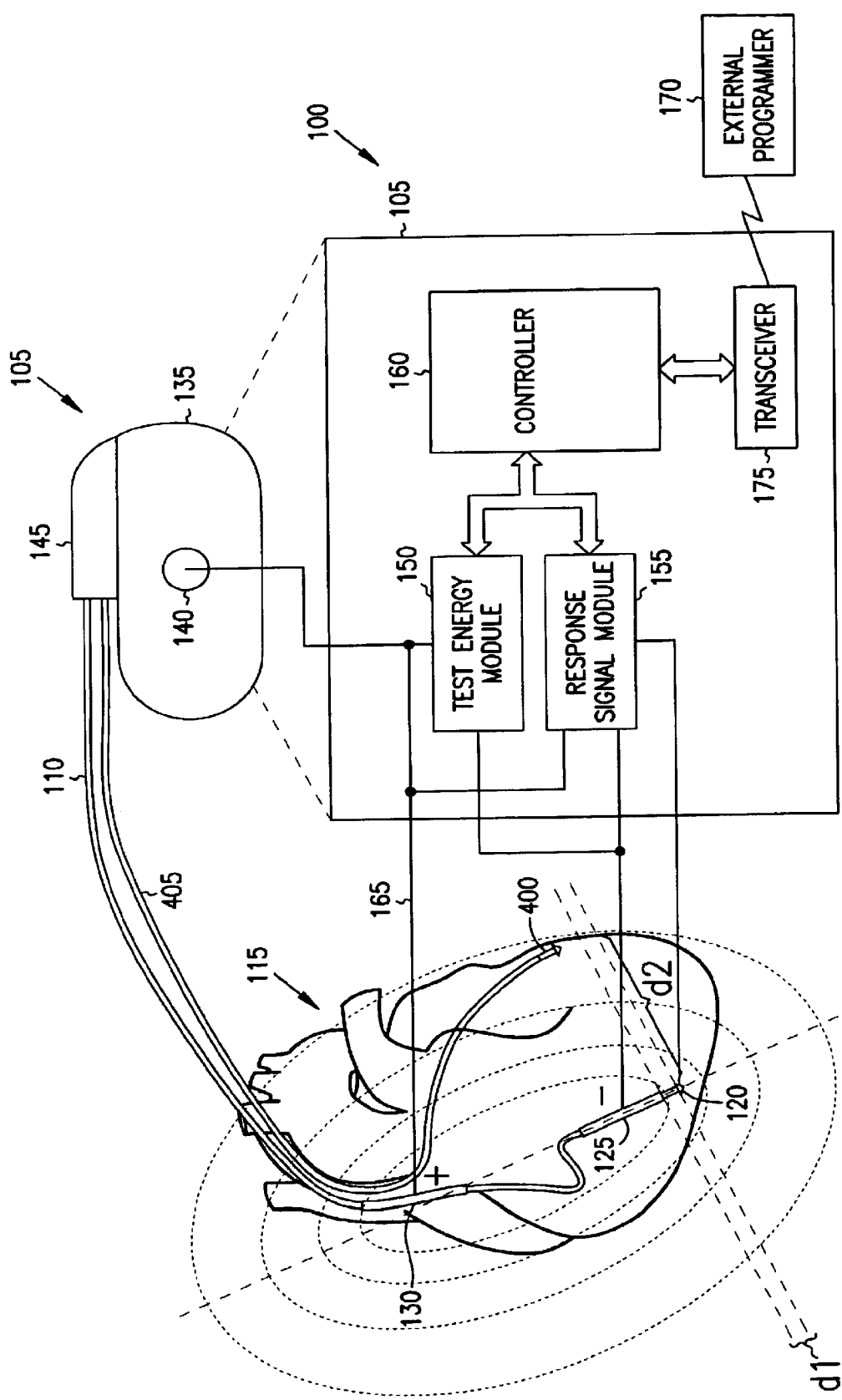
FIG. 4 is a schematic/block diagram illustrating an alternative embodiment of portions of the present cardiac rhythm management system that determines a distance from the defibrillation electrode without requiring fluoroscopic or other imaging.

FIG. 4 is a schematic/block diagram illustrating generally, by way of example, and not by way of limitation, another embodiment of portions of system 100 providing an alternate embodiment of determining the distance d2, such as described with respect to step 220 of FIG. 2, that does not require the use of fluoroscopic or other imaging. FIG. 4 includes an additional peripheral electrode 400 located at or close to the peripheral portion of the left ventricle (a distance d2 away from RV shock electrode 125) at which the predetermined electric field magnitude (e.g., 5 Volts/cm, as in the previous example) is desired during defibrillation. In one embodiment, this peripheral electrode 400 is introduced into the left ventricular periphery (e.g., coronary sinus and/or great cardiac vein) by an transvascular lead 405 through the right atrium and coronary sinus. In another embodiment, peripheral electrode 400 is a patch-type defibrillation electrode disposed on the exterior portion of the left ventricle. In either case, lead 405 may also include additional electrodes.

Figure 5:
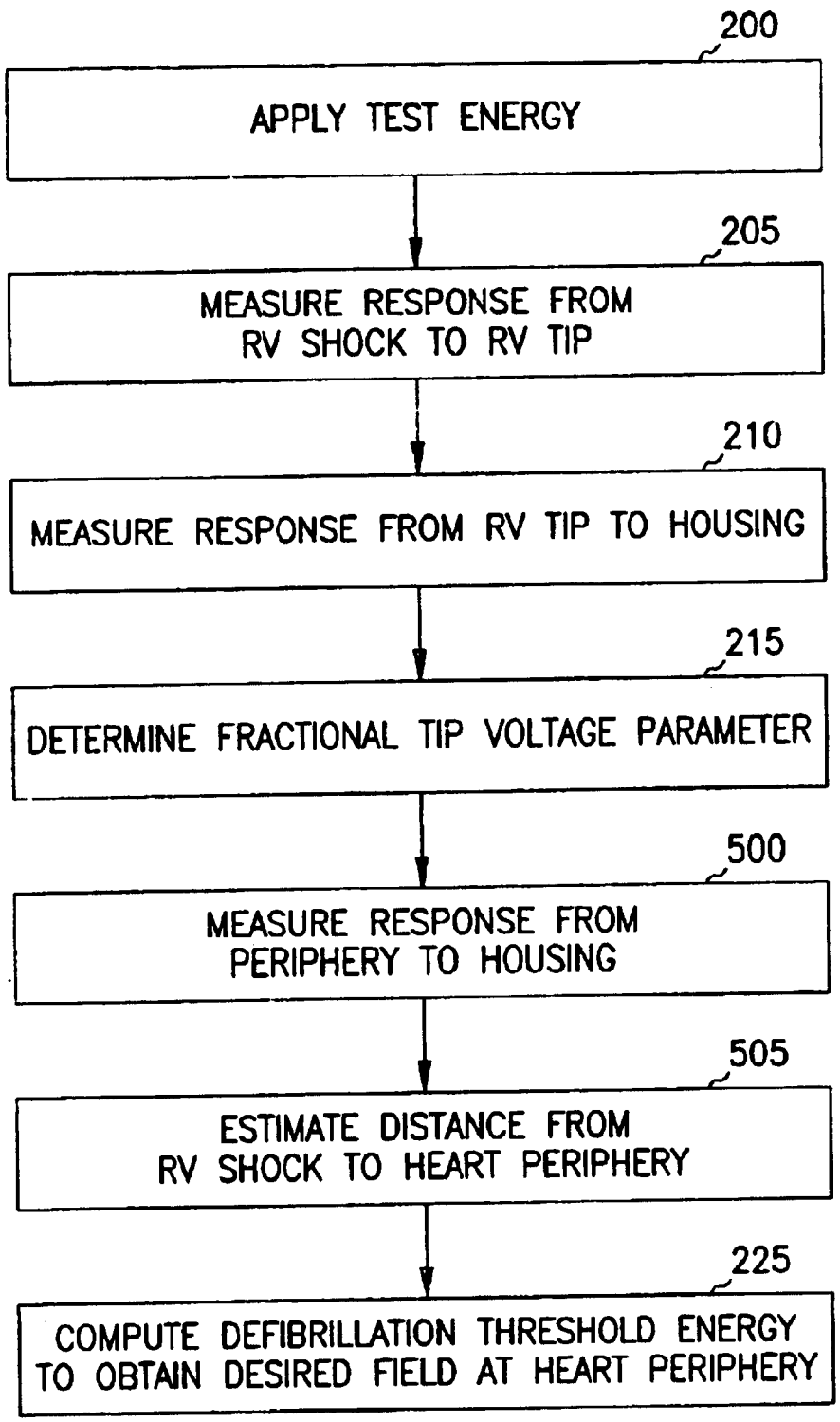
FIG. 5 is a flow chart, similar to that of FIG. 2, illustrating another method of operation such as using the system of FIG. 4.

FIG. 5 is a flow chart, similar to that of FIG. 2, illustrating generally, by way of example and not by way of limitation, another method of operation such as using the embodiment illustrated in FIG. 4. This technique is carried out by executable instructions, such as on controller 160, but it need not be carried out in the exact sequence indicated in FIG. 5. At step 500, an additional voltage measurement V3 is taken between peripheral electrode 400 and housing electrode 140 in response to the current delivered by test energy module 150 at step 200. At step 505 the distance d2 from RV shock electrode 125 to the heart periphery electrode 400 is estimated without relying on fluoroscopic or other imaging techniques to make a measurement. Instead, the distance d2 is estimated using the measured voltage V3 obtained in step 500.

Figure 6:
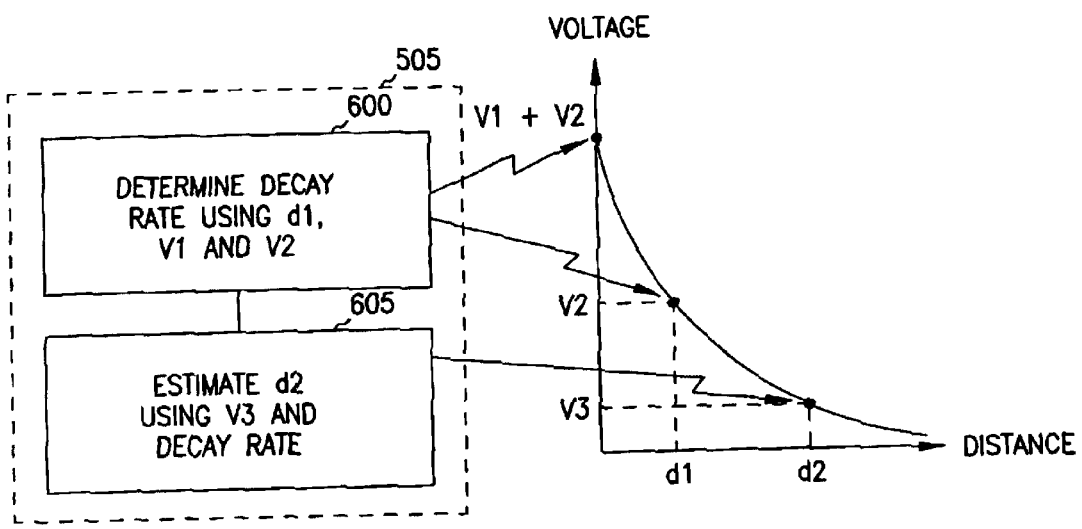
FIG. 6 is a flow chart and accompanying graph illustrating one technique for estimating a distance from an electrode.

FIG. 6 is a flow chart and accompanying graph illustrating generally, by way of example, but not by way of limitation, one technique for estimating the distance d2, at step 505. In this technique, the electric field near RV shock electrode 125 is approximated, as a function of distance, as a decaying exponential, for distances measured radially outward from RV shock electrode 125. By using (V1+V2) and V2 as points on this exponential curve that are separated by the known distance d1, as illustrated in FIG. 6, a decay rate "R" (i.e., the argument of the decaying exponential function) is computed at step 600. Then, at step 605, the distance d2 is estimated using the previously determined decay rate R. Having determined the distance d2 without relying on fluoroscopic imaging techniques, the defibrillation threshold energy is estimated as previously described herein with respect to FIGS. 1–3, or by other suitable technique.

OTHER EXAMPLES

Figure 7:
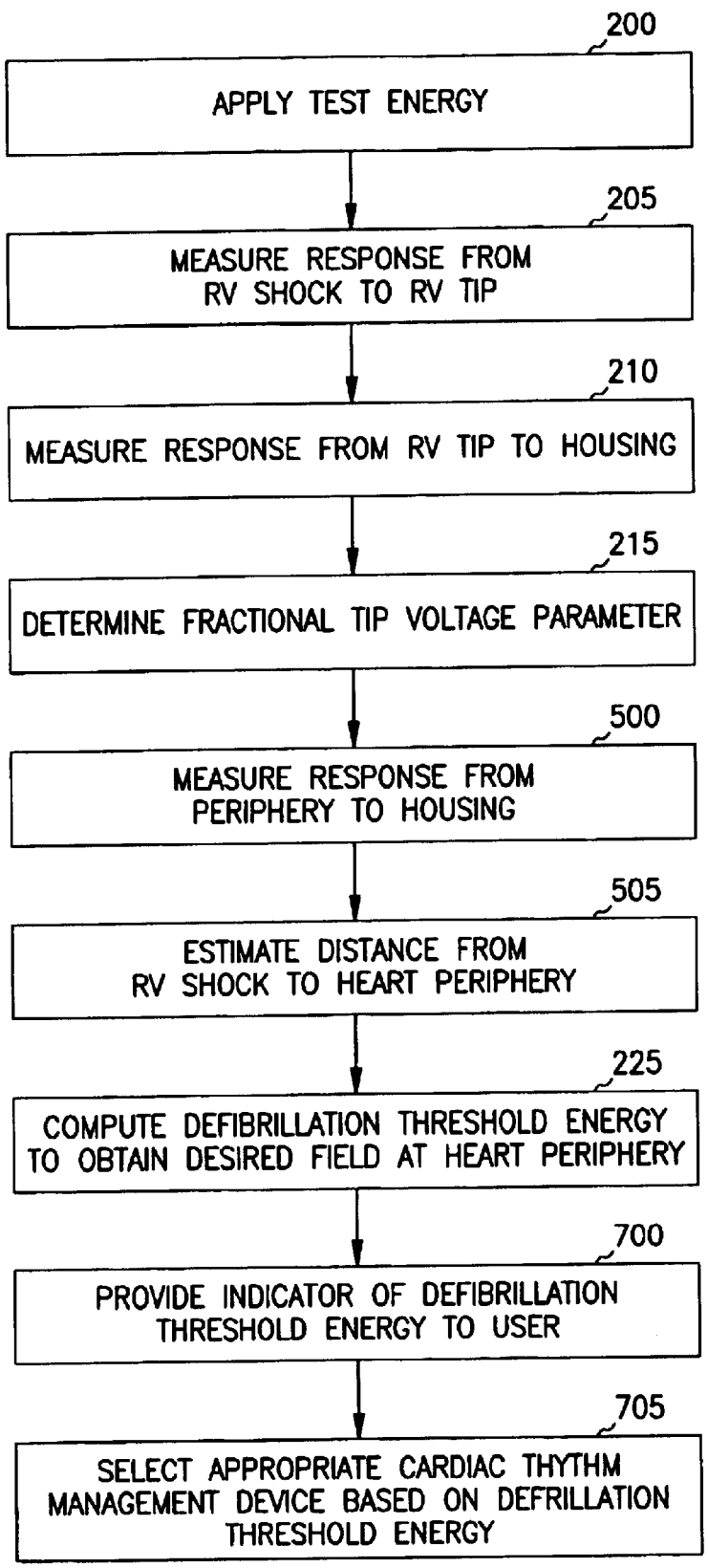
FIG. 7 is a flow chart illustrating another embodiment providing an indicator of the predicted defibrillation threshold and/or selecting an appropriate cardiac rhythm management device for implant.

FIG. 7 is a flow chart illustrating generally, by way of example, but not by way of limitation, another embodiment of using system 100. This embodiment includes steps for estimating defibrillation threshold voltages for a particular defibrillation waveform delivered from a particular electrode configuration, such as described with respect to FIG. 5 (or FIG. 2). Then, at step 700, an indication of the defibrillation threshold energy is provided to the user. In one example, the defibrillation threshold energy estimated within device 105 is communicated by telemetry transceiver 175 to external programmer 170 for display, such as on a computer monitor, audible output, printed means, or using any other indicator. In another example, the defibrillation threshold energy is estimated by hardware included within external programmer 170, which is itself coupled to lead 110 with or without actually implanting a device 105. A resulting indication of the defibrillation threshold energy is displayed on programmer 170. Based on this indicated defibrillation threshold energy, the user selects an appropriate cardiac rhythm management device 105 for implantation. In this way, an implantable cardiac rhythm management device 105 having a larger battery capacity is selected for a patient exhibiting a larger defibrillation threshold voltage than for a patient exhibiting a lesser defibrillation threshold voltage. This selection of a cardiac rhythm management device 105 having appropriate energy capacity may also be based on other factors, including, by way of example, but not by way of limitation, the expected frequency of needed defibrillation episodes, the patient's need for other power-consuming features in the implantable cardiac rhythm management device. Thus, according to this technique of computing defibrillation thresholds for a particular electrode configuration, the user may advantageously determine the appropriate cardiac rhythm management device 105 before actually performing an implantation.

Figure 8:
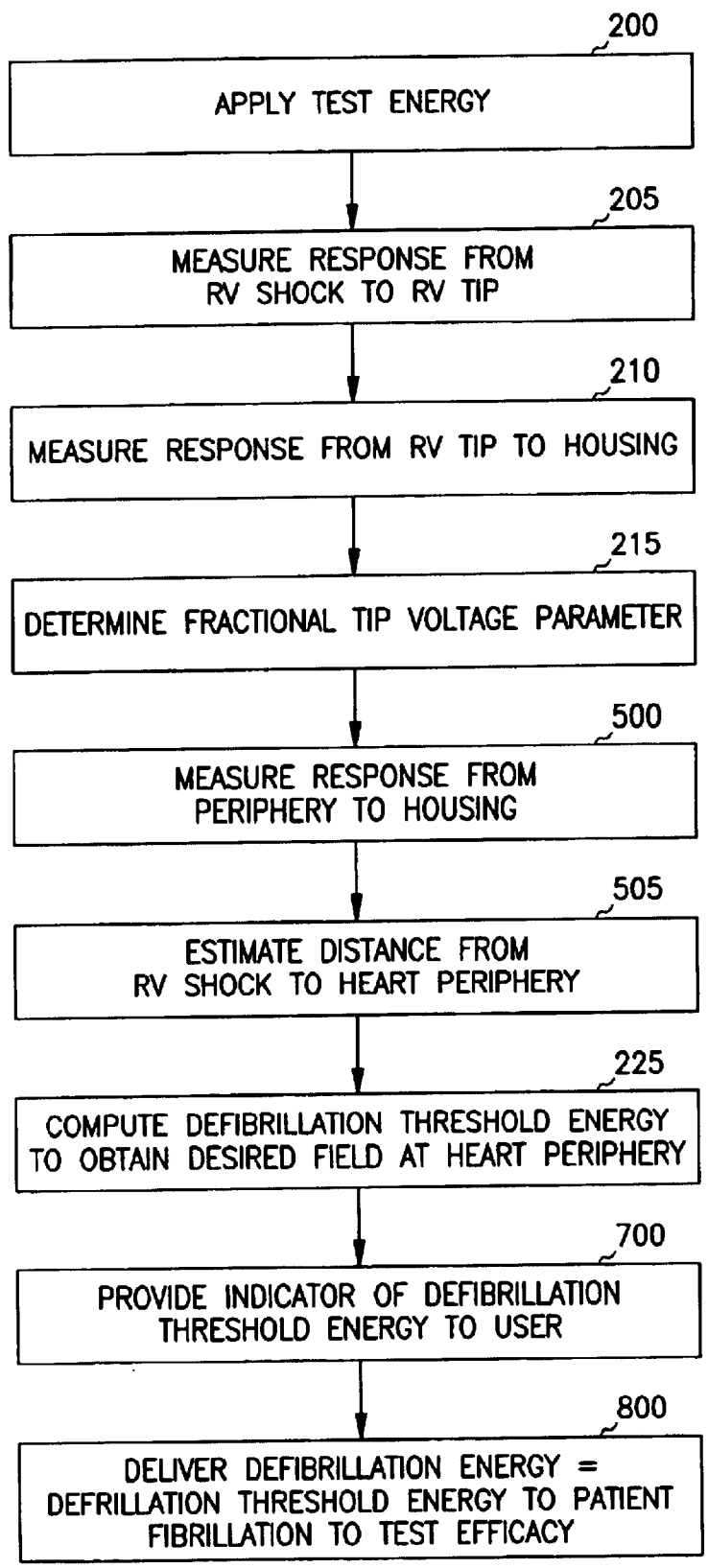
FIG. 8 is a flow chart illustrating another embodiment providing a defibrillation shock based on the predicted defibrillation threshold energy.

FIG. 8 is a flow chart illustrating generally, by way of example, but not by way of limitation, another embodiment of using system 100. This embodiment includes steps for estimating defibrillation threshold voltages for a particular defibrillation waveform and providing an indicator of the defibrillation threshold energy to the user, as described with respect to FIG. 7. Then, at step 800, a defibrillation shock having a magnitude based on the predicted defibrillation threshold energy (e.g., equal to the predicted defibrillation threshold energy) is delivered to a patient in fibrillation to test whether the applied defibrillation shock magnitude is sufficient to defibrillate the patient. If the defibrillation is successful, the user may again test efficacy using a lesser defibrillation shock; if the defibrillation is not successful, the user may again test efficacy using a greater defibrillation shock.

Figure 9:
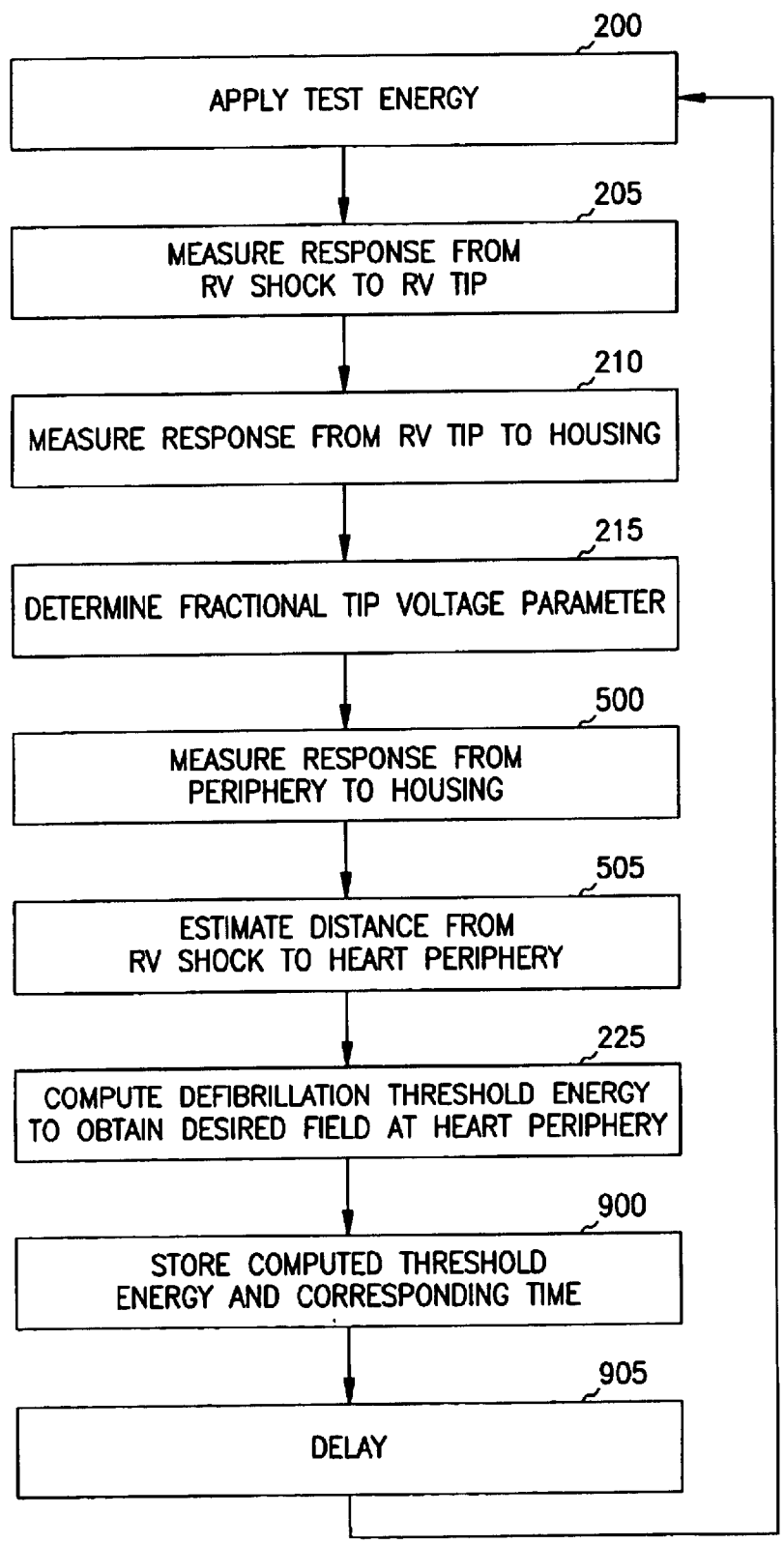
FIG. 9 is a flow chart illustrating another embodiment for recording acute or chronic computed defibrillation thresholds.

FIG. 9 is a flow chart illustrating generally, by way of example, but not by way of limitation, another embodiment of using system 100. This embodiment includes steps for estimating defibrillation threshold voltages for a particular defibrillation waveform (as described with respect to FIGS. 2 and 5). At step 900, the computed defibrillation threshold energy and corresponding time is stored in memory in controller 160. After a delay at step 905, the defibrillation threshold estimation steps are repeated and the resulting defibrillation threshold energy and time are again recorded and stored. The stored defibrillation threshold energy and corresponding time data is, in one embodiment, communicated to external programmer 170 by transceiver 175. In one embodiment, a relatively short delay (e.g., approximately between 1 hour and 1 day, inclusive) is used at step 905, during a period of time immediately following implantation of defibrillation lead 110. In this way, acute changes in defibrillation threshold are monitored and stored. In another embodiment, a longer delay (e.g., approximately between 1 day and 1 month, inclusive) is used at step 905. In this way, chronic changes in defibrillation threshold are monitored and stored. Such chronic changes in defibrillation threshold provide one indication of patient well-being and suitability for continued use of the cardiac rhythm management system 100.

FIG. 10 is a graph of transthoracic impedance (Z) versus time. FIG. 10 illustrates another aspect of the present system 100 in which a patient characteristic, such as breathing (also referred to as respiration or ventilation) is monitored. One technique for monitoring breathing is by measuring transthoracic impedance, as described in Hartley et al. U.S. Pat. No. 6,076,015 entitled "RATE ADAPTIVE CARDIAC RHYTHM MANAGEMENT DEVICE USING TRANSTHORACIC IMPEDANCE," assigned to Cardiac Pacemakers, Inc., which is incorporated herein by reference in its entirety. As illustrated in FIG. 10, defibrillation thresholds are repeatedly computed, according to the techniques described herein, at several different times during the patient's breathing cycle of inhaling and exhaling. An indication of the portion of the breathing cycle that corresponds to the lowest computed defibrillation threshold is recorded. In one example, this is implemented by recording a transthoracic impedance corresponding to the lowest defibrillation threshold. In another embodiment, this is implemented by recording a time delay from a fiducial point of the thoracic impedance waveform (e.g., maxima, minima, "zero"-crossing, etc.). Then, at some later time when the patient is in fibrillation, a defibrillation shock is delivered by system 100 synchronized to (among other things) the portion of the respiration cycle that was found to correspond to the lowest defibrillation threshold energy. In a broader sense, because the defibrillation threshold estimation techniques disclosed herein do not require an actual defibrillation energy or fibrillation-inducing energy, such defibrillation threshold estimation can be carried out repeatedly for evaluation over a range of any other patient characteristics (e.g., posture, etc.) besides breathing. Variations in the defibrillation threshold energy may then be used to synchronize delivery of the defibrillation shock to that particular patient characteristic, or to otherwise modify therapy delivery.

CONCLUSION

The above-discussed system provides, among other things, an apparatus and methods for estimating defibrillation thresholds without having to induce an arrhythmia or provide a defibrillation shock, and thereby avoids the disadvantages associated therewith, as discussed above. Although the system has been so described to illustrate this one of its advantages, it is not limited in this way. Stated differently, the system could also be used in conjunction with techniques that induce arrhythmias and/or deliver defibrillation countershocks to determine defibrillation thresholds.

The above-discussed system has been particularly described in terms of its use to determine ventricular defibrillation thresholds. However, it is understood that the described technique could also be used to determine atrial or other defibrillation thresholds by simply repositioning the electrodes to be associated with the atrial tissue to be defibrillated. Moreover, the described system need not be confined to a use in determining defibrillation thresholds; it could also be used for determining the required applied voltage at any electrode that is needed to obtain a desired electric field at a distance away therefrom.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the term "including" is used as being equivalent to the term "comprising," and its interpretation should not be limited to "physically including" unless otherwise indicated.

What is claimed is:

1. A method including:
   delivering a nondefibrillating and nonfibrillation-inducing test energy to a heart;
   detecting a resulting output signal based on the test energy and a heart characteristic;
   estimating a defibrillation threshold, based on the output signal, for a portion of the heart to be defibrillated; and
   in which delivering the test energy to the heart includes delivering a continuous or pulsed carrier signal to the heart.

2. The method of claim 1, in which the carrier signal frequency is greater than or equal to 1 kiloHertz.

3. The method of claim 2, in which the carrier signal frequency is less than or equal to 100 kiloHertz.

4. The method of claim 1, further including:
   providing first and second electrodes for delivering the test energy to the heart;
   providing third and fourth electrodes for detecting the resulting output signal based on the test energy and the heart characteristic; and
   in which at least one of the third and fourth electrodes is an electrically different electrode from the first and second electrodes.

5. The method of claim 4, in which at least one of the third and fourth electrodes is electrically in common with one of the first and second electrodes.

6. The method of claim 5, in which at least one of the third and fourth electrodes is the same electrode as one of the first and second electrodes.

7. The method of claim 1, in which the heart characteristic includes an electric field associated with a voltage drop across first and second locations in the heart.

8. The method of claim 1, further including providing a user with the estimated defibrillation threshold.

9. A method including:
   delivering a nondefibrillating and nonfibrillation-inducing test energy to a heart;
   detecting a resulting output signal based on the test energy and a heart characteristic; and
   estimating a defibrillation threshold, based on the output signal, for a portion of the heart to be defibrillated, in which estimating the defibrillation threshold includes comparing the heart characteristic to a desired value.

10. The method of claim 9, further including selecting the desired value of the heart characteristic to ensure a desired value of electric field associated with the portion of the heart to be defibrillated.

11. A method including:
    delivering a nondefibrillating and nonfibrillation-inducing test energy to a heart;
    detecting a resulting output signal based on the test energy and a heart characteristic;
    estimating a defibrillation threshold, based on the output signal, for a portion of the heart to be defibrillated; and
    selecting a cardiac rhythm management device for implantation based on the estimated defibrillation threshold and an energy capability of the cardiac rhythm management device.

12. A method including:
    delivering a nondefibrillating and nonfibrillation-inducing test energy to a heart;
    detecting a resulting output signal based on the test energy and a heart characteristic;
    estimating a defibrillation threshold, based on the output signal, for a portion of the heart to be defibrillated; and
    delivering a test defibrillation pulse based on the estimated defibrillation threshold.

13. The method of claim 12, further including delivering a series of test defibrillation pulses in which an energy of the first test defibrillation pulse in the series is based on the estimated defibrillation threshold.

14. A method including:
    delivering a nondefibrillating and nonfibrillation-inducing test energy to a heart;
    detecting a resulting output signal based on the test energy and a heart characteristic;
    estimating a defibrillation threshold, based on the output signal, for a portion of the heart to be defibrillated; and
    repeating the aforementioned steps over a period of time that is long enough to detect changes in acute defibrillation thresholds.

15. A method including:
    delivering a nondefibrillating and nonfibrillation-inducing test energy to a heart;
    detecting a resulting output signal based on the test energy and a heart characteristic;
    estimating a defibrillation threshold, based on the output signal, for a portion of the heart to be defibrillated; and repeating the aforementioned steps over a period of time that is long enough to detect changes in chronic defibrillation thresholds.

16. A method including:

delivering a nondefibrillating and nonfibrillation-inducing test energy to a heart;

detecting a resulting output signal based on the test energy and a heart characteristic;

estimating a defibrillation threshold, based on the output signal, for a portion of the heart to be defibrillated;

sensing a different patient characteristic from that existing during the steps of delivering, detecting, and estimating; and repeating the steps of delivering, detecting, and estimating during a time period that includes the sensing the different patient characteristic.

17. The method of claim 16, in which sensing the different patient characteristic includes sensing a portion of a respiration cycle, and the step of repeating includes repeating the steps of delivering, detecting, and estimating during a different portion of the respiration cycle.

18. The method of claim 17, further including synchronizing delivery of therapy to a portion of the respiration characteristic that corresponds to a lower estimated defibrillation threshold over the respiration cycle than another defibrillation threshold over a different portion of the respiration cycle.

19. The method of claim 16, further including synchronizing delivery of therapy to a portion of the patient characteristic that corresponds to a lower estimated defibrillation threshold than another defibrillation threshold over a different portion of the patient characteristic.

20. A method of determining a defibrillation threshold energy, the method including:

positioning a first electrode near a heart at a predetermined distance, d1, from a second electrode near the heart;

providing a predetermined nondefibrillating and nonfibrillation-inducing test energy, in a heart between the first electrode and a third electrode;

detecting a resulting first response, V1, between the first and second electrodes;

detecting a resulting second response, V2, between the first and third electrodes;

determining an electric field near the second electrode based on V1 and V2;

measuring a distance, d2, between the second electrode and a distal portion of the heart tissue to be defibrillated; and estimating the defibrillation threshold energy, based on a predetermined required defibrillation electric field at the distal portion of the heart tissue to be defibrillated, d2, and the electric field near the second electrode.

21. The method of claim 20, in which measuring the distance, d2, includes fluoroscopically determining d2.

22. The method of claim 21, in which fluoroscopically determining d2 includes assessing d2 based on a known fluoroscopically viewable distance.

23. The method of claim 22, in which fluoroscopically determining d2 includes assessing d2 based on a known fluoroscopically viewable distance d1 between the first and second electrodes.

24. The method of claim 20, in which measuring the distance, d2, includes:

detecting a resulting third voltage, V3, between a fourth electrode and the third electrode;

estimating a decay rate, R, using V1, V2 and the known distance d1 between the first and second electrodes; and estimating d2 based on V3 and R.

25. A method of determining a defibrillation threshold energy, the method including:

positioning a right ventricular (RV) tip electrode in a heart at a predetermined distance, d1, from an RV shock electrode in the heart;

positioning a superior vena cava (SVC) electrode in or near the heart;

providing a nondefibrillating and nonfibrillation-inducing predetermined test current in a heart between the RV shock electrode and a cardiac rhythm management device housing electrode that is electrically connected in common with the SVC electrode;

detecting a resulting first voltage, V1, between the RV tip electrode and the RV shock electrode;

detecting a resulting second voltage, V2, between the RV tip electrode and the commonly connected SVC and housing electrodes;

determining a fractional tip voltage parameter as V2/(V1+V2);

measuring a distance, d2, between the RV shock electrode and a left ventricular apical heart periphery; and estimating the defibrillation threshold energy, based on a predetermined required defibrillation electric field at the left ventricular apical heart periphery, d2, and the fractional tip voltage parameter and an elliptical model of dipolar electric field distribution having the RV shock and SVC electrodes as its foci.

26. The method of claim 25, in which measuring the distance, d2, includes fluoroscopically determining d2.

27. The method of claim 26, in which fluoroscopically determining d2 includes assessing d2 using a known fluoroscopically viewable distance.

28. The method of claim 27, in which fluoroscopically determining d2 includes assessing d2 using the known fluoroscopically viewable distance d1.

29. The method of claim 25, in which measuring the distance, d2, includes:

detecting a resulting third voltage, V3, between a left ventricular (LV) apical peripheral electrode and the commonly connected SVC and ICD housing electrodes;

estimating an exponential decay rate, R, using V1, V2, and the known distance d1; and estimating the distance d2 based on V3 and R.

30. A system including:

first and second electrodes configured for association with a heart;

a test energy module, coupled to the second electrode, for delivering a nondefibrillating and nonfibrillation-inducing test energy to the heart;

a response signal module, coupled to the first and second electrodes for detecting responses to the test energy; and a controller, coupled to the response signal module, the controller including a module estimating a defibrillation threshold energy based on a predetermined desired defibrillation electric field at a distal portion of the heart tissue to be defibrillated and a distance from the second electrode to the distal portion of the heart tissue, and an indication of the electric field near the second electrode.

31. The system of claim 30, in which the first and second electrodes are configured for association with a right ventricle of the heart.

32. The system of claim 31, in which the first electrode includes a macroscopic surface area that is approximately between 1 mm$^2$ and 20 mm$^2$, inclusive.

33. The system of claim 30, in which the first electrode is selected from a group consisting of a tip electrode and a ring electrode.

34. The system of claim 30, in which the second electrode includes a shock electrode.

35. The system of claim 30, in which the second electrode includes a coil electrode.

36. The system of claim 30, in which the test energy module includes a test current source.

37. The system of claim 36, in which the test current source includes a carrier signal.

38. The system of claim 37, in which the carrier signal has a frequency that is approximately between 1 kHz and 100 kHz, inclusive.

39. The system of claim 37, in which the carrier signal is continuous.

40. The system of claim 37, in which the carrier signal is pulsed.

41. The system of claim 37, in which the response signal module includes a demodulater for demodulating a detected response to a portion of the carrier signal.

42. The system of claim 30, in which the controller includes executable instructions determining an electric field near the second electrode based on voltages measured at the first and second electrodes and a known distance between the first and second electrodes.

43. The system of claim 42, in which the controller includes executable instructions determining an electric field near the distal portion of the heart tissue based on the electric field near the second electrode and a distance between the second electrode and the distal portion of the heart tissue.

44. The system of claim 43, in which the controller includes executable instructions for determining the defibrillation threshold energy based on scaling the voltage measured at the second electrode by a ratio of the desired electric field at the distal portion of the heart tissue to the previously determined electric field near the distal portion of the heart tissue.

45. A system including:
first, second, and third electrodes configured for association with a heart, in which the first and second electrodes are separated by a predetermined distance;
a test energy module, coupled to the second and third electrodes, for delivering therebetween a nondefibrillating and nonfibrillation-inducing test energy to the heart;
a response signal module, coupled to the first and second electrodes for detecting responses to the test energy; and
a defibrillation threshold energy estimation module, coupled to the response signal module, and estimating a defibrillation threshold energy based on a predetermined desired defibrillation electric field at a distal portion of the heart tissue to be defibrillated, a distance from the second electrode to the distal portion of the heart tissue, and an indication of the electric field near the second electrode obtained by measuring the response signal at the first and second electrodes and by using the predetermined separation between the first and second electrodes.

46. A system including:
first, second, and third electrodes configured for association with a heart, in which the first and second electrodes are separated by a known predetermined distance;
a test energy module, coupled to the second and third electrodes, for delivering therebetween a nondefibrillating and nonfibrillation-inducing test energy to the heart;
a response signal module, coupled to the first and second electrodes for detecting responses to the test energy; and
means, coupled to the response signal module, for estimating the defibrillation threshold energy using the known predetermined distance.

47. A cardiac rhythm management system including:
a first right ventricular (RV) electrode, a second RV electrode, a superior vena cava (SVC) electrode, and a housing electrode, configured for association with a heart; and
a cardiac rhythm management (CRM) device, coupled to the electrodes, the CRM device including:
a test energy module, delivering a nondefibrillating and nonfibrillation-inducing test energy to the heart;
a response signal module, coupled to the first and second RV electrodes for detecting a response to the test energy; and
a defibrillation threshold energy estimation module, coupled to the response signal module, and estimating a defibrillation threshold energy based on: (a) a predetermined desired defibrillation electric field at portion of the heart tissue to be defibrillated that is distal to the second RV electrode; (b) a distance from the second electrode to the distal portion of the heart tissue; (c) an indication of the electric field near the second electrode obtained by measuring the response signal at the first and second electrodes and by using the predetermined separation between the first and second electrodes.

48. The system of claim 47, in which the housing electrode and the SVC electrode are electrically connected in common.

49. A method including:
delivering a nondefibrillating carrier signal test energy to a heart;
detecting a resulting output signal based on the test energy and a heart characteristic; and
estimating a defibrillation threshold, based on the output signal, for a portion of the heart to be defibrillated.

50. The method of claim 49, in which the estimating the defibrillation threshold includes comparing the heart characteristic to a desired value.

51. The method of claim 49, further including selecting a desired value of the heart characteristic to ensure a desired value of electric field associated with the portion of the heart to be defibrillated.

52. The method of claim 49, further including selecting a cardiac rhythm management device for implantation based on the estimated defibrillation threshold and an energy capability of the cardiac rhythm management device.

53. The method of claim 49, further including providing a user with the estimated defibrillation threshold.

54. The method of claim 49, further including:
sensing a different patient characteristic from that existing during the acts of delivering, detecting, and estimating; and
repeating the acts of delivering, detecting, and estimating during a time period that includes the sensing the different patient characteristic.

55. The method of claim 54, in which sensing the different patient characteristic includes sensing a portion of a respiration cycle, and the step of repeating includes repeating the steps of delivering, detecting, and estimating during a different portion of the respiration cycle.

56. The method of claim 55, further including synchronizing delivery of therapy to a portion of the respiration characteristic that corresponds to a lower estimated defibrillation threshold over the respiration cycle than another defibrillation threshold over a different portion of the respiration cycle.

57. The method of claim 54, further including synchronizing delivery of therapy to a portion of the patient characteristic that corresponds to a lower estimated defibrillation threshold than another defibrillation threshold over a different portion of the patient characteristic.

* * * * *